United States Patent [19]

McConaghy, Jr. et al.

[11] 3,940,429

[45] Feb. 24, 1976

[54] OXIDATION OF UNSATURATED AMINES

[75] Inventors: John S. McConaghy, Jr.; Dennis C. Owsley, both of St. Louis, Mo.

[73] Assignee: Monsanto Company, St. Louis, Mo.

[22] Filed: Dec. 9, 1974

[21] Appl. No.: 530,930

[52] U.S. Cl..... 260/465.9; 260/283 CN; 260/294.9; 260/940; 260/464; 260/465 R; 260/465.4; 260/465.6
[51] Int. Cl.$^2$........................................ C07C 120/00
[58] Field of Search.......... 260/465.9, 465 K, 465 R

[56] References Cited
UNITED STATES PATENTS

| | | | |
|---|---|---|---|
| 2,375,015 | 5/1945 | Marple et al. | 260/465.9 |
| 2,375,016 | 5/1945 | Marple et al. | 260/465.9 |
| 2,471,927 | 5/1949 | Bortnick et al. | 260/465.9 |
| 2,849,478 | 8/1958 | Zubay et al. | 260/465.9 X |
| 3,719,701 | 3/1973 | Bach | 260/465.9 |

*Primary Examiner*—Joseph Paul Brust
*Attorney, Agent, or Firm*—James C. Logomasini; Paul L. Passley

[57] ABSTRACT

Oxidation of an unsaturated amine to an unsaturated nitrile is carried out in presence of cuprous chloride, a nitrogen base and a halide salt soluble in the nitrogen base.

8 Claims, No Drawings

OXIDATION OF UNSATURATED AMINES

BACKGROUND OF THE INVENTION

Polymers derived from unsaturated nitrile monomers such as acrylonitrile, methacrylonitrile, vinylidene cyanide, etc., are well known in the art. Of this class of monomers, acrylonitrile is presently the most important and is used in making a variety of commercial products e.g., butadiene-acrylonitrile copolymer rubbers, acrylonitrile-butadiene-styrene (ABS) copolymers and acrylic textile fibers.

Several means of producing acrylonitrile have been proposed including dehydration of ethylene cyanohydrin, the direct reaction of acetylene and hydrogen cyanide and the catalytic amination of propylene followed by dehydrogenation of the proprionitrile so produced.

One of the more effective routes that is widely practised is the catalytic ammoxidation of propylene.

These processes, however, have the disadvantage of producing troublesome by-products and some, particularly the last mentioned, require the use of very expensive high pressure and high temperature equipment.

A further alternate process was disclosed in British Patent Specification No. 570,835 granted to Shell Development Company on July 25, 1945. This process is one for the production of unsaturated nitriles from the corresponding unsaturated amine by reacting the amine with oxygen in the presence of a silver oxidation catalyst at a temperature of at least 450°C. The process is essentially a vapor phase reaction in which a mixture of the amine vapor, oxygen and an inert carrier gas are passed over a metal-alloy catalyst bed at about 500°C. This process has the disadvantage of requiring expensive and complex equipment and high temperatures.

A further development of the route from unsaturated amine to unsaturated nitrile is provided in U.S. Pat. No. 3,719,701 in which the amine is reacted with molecular oxygen in a solvent containing cuprous and cupric ions, the solvent being a nitrogen base. This process has many advantages in its simplicity, its relative freedom from undesirable by-products and its adaptability to continuous operation. It does, however, have the disadvantage that the yields obtained are quite low, the figure given for the conversion of allylamine to acrylonitrile using a cuprous chloride catalyst being 43.8%.

We have now discovered a process for the production of unsaturated nitriles by oxidation of the corresponding unsaturated amines in which the yields are substantially improved over those described for the corresponding reaction in U.S. Pat. No. 3,719,701 while retaining the many advantages inherent in such a process.

Accordingly, it is an object of this invention to provide a simple, economic process for the production of unsaturated nitriles.

It is also an object of this invention to provide a process for the preparation of unsaturated nitriles from corresponding unsaturated amines in high yields and substantially free of undesirable by-products.

Other objects and advantages of the invention will become apparent from the following detailed description.

SUMMARY OF THE INVENTION

The process of the present invention is one for the conversion of an unsaturated amine to an unsaturated nitrile which comprises contacting an unsaturated amine with oxygen in the presence of a mixture consisting essentially of a nitrogen base, cuprous chloride and a halide salt which is soluble in the nitrogen base, at a temperature of from 0° to 200°C.

The unsaturated amine used in the process of the invention is most conveniently one having the formula:

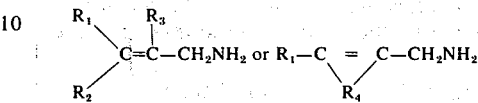

wherein $R_1$, $R_2$ and $R_3$ represent hydrogen or monovalent organic radical and $R_4$ represents a divalent organic radical, with the limitation that such radicals are not oxidizable and do not inactivate the catalyst under the reaction conditions used in the process.

Monovalent organic radicals of this description include alkyl, olefinically unsaturated aliphatic, cycloaliphatic, alkaryl, aromatic, heteroaromatic and halogenated hydrocarbon radicals, (e.g., chlorinated and brominated hydrocarbon radicals), and radicals of the formula:

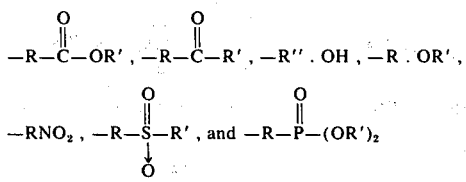

wherein R represents a divalent hydrocarbon radical, such as alkylene or phenylene, R' represents a monovalent hydrocarbon radical, such as alkyl or phenyl, and R'' is alkylene or an olefinically unsaturated divalent radical. Representative monovalent radicals include:

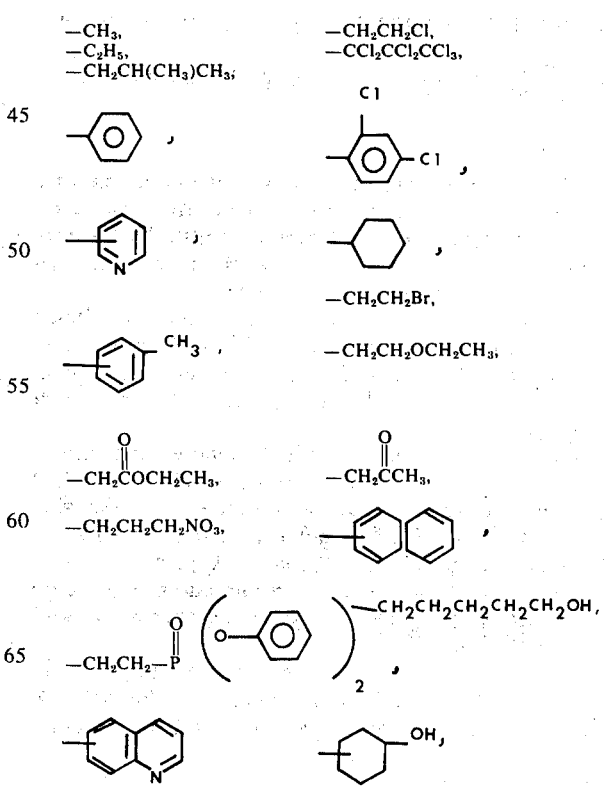

Divalent radicals of the foregoing description, i.e., $R^4$, include: $-CH=CH-CH=CH-$, $-CH_2CH_2CH_2CH_2$, $-CH=N-CH=CH-$, $-O-CH=CH-CH_2-$, $-CH_2-CH=CH-$, and the like.

Generally, the unsaturated amines used in carrying out the process of the invention contain from 3 to 24 carbon atoms. Typical examples of such unsaturated amines and the corresponding unsaturated nitriles prepared therefrom by the process of the invention are:

A  $CH_2=CHCH_2NH_2$ a  $CH_2=CHC\equiv N$

B  $CH_2=\underset{\underset{CH_3}{|}}{C}-CH_2NH_2$ b  $CH_2=\underset{\underset{CH_2}{|}}{C}-C\equiv N$ C  $CH_3\underset{\underset{CH_3}{|}}{C}HCH=CHCH_2NH_2$ c  $CH_3\underset{\underset{CH_3}{|}}{C}HCH=CHC\equiv N$ D  $CH_3\underset{\underset{CH_3}{|}}{\overset{\overset{CH_3}{|}}{C}}CH=CHCH_2NH_2$ d  $CH_3\underset{\underset{CH_3}{|}}{\overset{\overset{CH_3}{|}}{C}}CH=CHC\equiv N$ E  $CH_3\underset{\underset{CH_3}{|}}{\overset{\overset{CH_3}{|}}{C}}CH_2CH=CHCH_2NH_2$ e  $CH_3\underset{\underset{CH_3}{|}}{\overset{\overset{CH_3}{|}}{C}}-CH_2CH=CHC\equiv N$ F  phenyl-$CH_2NH_2$ f  phenyl-$C\equiv N$

G  $CH_3CH_2OCH\ CHCH_2NH_2$ g  $CH_3CH_2OCH\ CHC\equiv N$

H  8-aminoquinoline ($H_2NCH_2$ on quinoline)

h  quinoline-$N\equiv C$

I  pyridyl-$CH_2NH_2$ i  pyridyl-$C\equiv N$

J  $HOCH_2CH_2CH=CHCH_2NH_2$ j  $HOCH_2CH_2CH=CHC\equiv N$

K  cyclohexenyl-$CH_2NH_2$ k  cyclohexenyl-$C\equiv N$

The amine reactant may consist of one amine or a mixture of amines. For example, benzonitrile and acrylonitrile may be prepared simultaneously by the process described herein by using, as the reactant, a mixture of benzylamine and allylamine.

The unsaturated amines useful in carrying out the process may be prepared by well known procedures described in the literature, e.g., by reacting the corresponding unsaturated halide, preferably the chloride or bromide with ammonia.

In carrying out the process defined herein the unsaturated amine reactant, as previously indicated, must not contain substituent groups which either are oxidizable or inactivate the catalyst under the process conditions. In this context oxidizable groups are primary or secondary amine groups, ethynyl groups and groups which inactivate the catalyst are acid groups, such as carboxy and sulfo groups.

The catalyst comprises a mixture of a nitrogen base, cuprous chloride and a halide soluble in the nitrogen base. The base and the cuprous chloride form a complex and the activity of this catalytic complex is modified by the presence of the halide. The halide salt can often be an alkali metal or alkaline earth metal halide. Among the halides the chloride and bromide are usually the most effective. The most convenient metal component of the halide is lithium so that, where the halide is a metal salt it is usually lithium chloride or lithium bromide. However, organic salts having a halide ion such as quaternary ammonium and phosphonium halides, e.g., tetra butyl ammonium chloride, tetra methyl phosphonium bromide and the like may also be used.

The term "nitrogen base" is used herein to indicate an organic nitrogen compound containing a nitrogen compound having an unshared pair of electrons which can combine with a proton. All nitrogen bases which are not oxidized by cupric ions may be used and a list of such compounds can be readily prepared by a man skilled in the art. As specific examples of such compounds, the following are cited: hexamethylphosphoramide, N,N-dimethylacetamide, N,N-dimethylformamide, N,N-dimethylpropionamide, N,N-diethylacetamide, N-methylpyrrolidone, N-ethylpyrrolidone, triethylamine, tributylamine, diethylmethylamide, N,alkylpiperidines, quinolines, isoquinolines, N-alkylmorpholines, and pyridine. Of these bases pyridine is generally preferred. Mixtures of bases may also be used in the process of the invention.

In the usual practice of the invention, the nitrogen base functions also as the reaction medium, but this is not an essential feature of the process. In some cases, therefore, it might be preferred to use a reaction medium distinct from the nitrogen base. Suitable reaction media are those which are solvents for the nitrogen base, the cuprous chloride and the soluble halide salt and which do not interfere with the catalyst and are not oxidized to any appreciable extent thereby.

The proportions of the components of the mixture of cuprous chloride and soluble halide can vary widely but in general the molar ratio of cuprous chloride to soluble halide can be from 10:1 to 1:10 such as from about 2:1 to 1:3 and preferably about 1:1. The amount of nitrogen base can also vary within wide limits so that the minimum possible (when the base does not form the reaction medium) is that necessary to complex the cuprous chloride. When the base also provides the reaction medium the amount used can of course be much greater.

The process can be operated at atmospheric or superatmospheric pressures and it is found that in many cases the use of pressures up to 500 psig confers substantial advantages. Within this range, pressures of 100 to 400 psig are preferred.

The temperature at which the reaction is conducted can be from 0° to 200°C. but in general temperatures of from 25 to 75°C. are satisfactory.

The catalyst can conveniently be prepared by adding the cuprous chloride and the halide salt to the nitrogen base (and optionally an inert solvent) with stirring, then treating with oxygen until oxygen uptake ceases.

In a preferred mode of operation, molecular oxygen is used as the primary oxidant and may be introduced into the reaction medium by diffusion or injection techniques. Pure oxygen may be used, or alternatively, air or other gases containing free oxygen may be used as the oxidant. To obtain optimum yields of the desired nitrile products, a molar ratio of oxygen to amine of at least one is used and, preferably, a molar excess of oxygen to amine is used. However, higher or lower ratios may be used, if desired, since unreacted amine can be recovered and, thus, the yield of nitrile is substantially unaffected by using an excess of amine to oxygen.

When the batch process is used, the catalyst system may be prepared as indicated above, preferably at room temperature or above, and the unsaturated amine added thereto under an atmosphere of oxygen with stirring for a period of time sufficient to ensure complete reaction. In this respect, a gas chromatograph has been found to be an excellent means for following the progress of the reaction. After completion, the nitrile product may be separated from the reaction mixture by distillation.

Alternatively the catalyst, prepared in the manner previously described, can be added to a chilled solution of the unsaturated amine in an appropriate reaction medium (e.g., the nitrogen base used to prepare the catalyst) and then oxygen added to the reaction medium until approximately the theoretical volume thereof has been consumed. This can be measured with great accuracy by using a closed system and a gas buret.

When the continuous process is used, it is preferable that the cuprous chloride/halide salt/nitrogen base complex be prepared first (with or without an inert solvent) and the unsaturated amine added thereto. The amine is added at a slow rate to the reaction mixture while simultaneously passing a stream of air, other oxidant gas mixture or molecular oxygen through the solution at a temperature and flow rate such that optimum reaction conditions are established with respect to nitrile product formation and the removal thereof from the reaction mixture by the gas sweep. The product is then removed from the exit gas stream by any well known method. The water formed as a result of the oxidation reaction may be removed from the nitrile by any suitable means such as by fractionation or the use of drying agents.

In actual operation, the optimum reaction conditions to be used in carrying out the process will depend on the reactants used, the oxidant vapor, and whether the continuous or batch method is employed. The optimum conditions for a given specific reaction and method can be readily determined by a few preliminary experiments.

To further illustrate the invention the following examples are given:

EXAMPLE I

This Example illustrates the improvement obtained in the activity of a cuprous chloride catalyst by addition thereto of lithium chloride.

A flask was equipped with a gas uptake measuring buret filled with oxygen. Pyridine (20 ml) and cuprous chloride (0.50 gram) were introduced into the flask and oxygen was added from the buret. At room temperature the solution took up 31 ml of oxygen. The temperature was then raised to 50°C. and 0.285 gram of allylamine were added. After 2 hours a yield of 32% AN was obtained.

A second run was performed in exactly the way described above except that 0.43 gram of lithium chloride was added to the cuprous chloride and pyridine. After 2 hours of reaction the yield of acrylonitrile was found to be 60%.

EXAMPLE II

This Example illustrates the improvement obtained in the activity of a cuprous chloride catalyst by addition thereto of lithium bromide.

A catalyst was prepared as described in Example I with the difference that only 0.1 gram of cuprous chloride was used.

The yield of acrylonitrile when the catalyst was used to prepare acrylonitrile by the process described in Example I was 18%.

When .087 gram of lithium bromide was added to the catalyst composition and the catalyst was used to prepare acrylonitrile by the method described above, the yield of acrylonitrile was raised to 38%.

EXAMPLE III

This Example illustrates the improvement in activity obtained by the addition of tetrabutylammonium chloride to a cuprous chloride catalyst.

In an experiment similar to that described in the second run of Example I, 2.78 grams of tetrabutylammonium chloride were added in place of the lithium chloride.

After 2 hours the yield of acrylonitrile was found to be 60%.

EXAMPLE IV

This Example illustrates the improvement in activity obtained by the addition of tetrabutylammonium bromide to a cuprous chloride catalyst.

In an experiment similar to that described in the second run of Example II, 0.312 gram of tetrabutylammonium bromide was substituted for the lithium bromide.

After 2 hours the yield of acrylonitrile was found to be 32%.

It will be obvious to one skilled in the art that sundry modifications of the above process could be devised and it is intended that all such modifications shall be included as fall within a reasonable interpretation of the claims appended hereto.

What is claimed is:

1. A process for the production of an unsaturated nitrile which comprises reacting an unsaturated amine having the formula

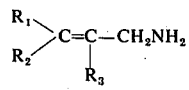

or phenyl—$CH_2NH_2$ wherein $R_1$, $R_2$ and $R_3$ represent hydrogen or a $C_1$ to $C_4$ alkyl group with molecular oxygen in the presence of cuprous chloride, a nitrogen base that is not oxidized under the reaction conditions and a halide salt which is soluble in the nitrogen base and is selected from alkali metal halides, alkaline earth metal halides, quaternary ammonium halides, and phosphonium halides, the relative proportions of cuprous chloride and halide salt being from 1:10 to 10:1, at a temperature of from 0° to 200°C. and at atmospheric pressure or above.

2. A process according to claim 1 in which the unsaturated amine is allylamine or methallylamine and the unsaturated nitrile produced is acrylonitrile or methacrylonitrile.

3. A process according to claim 2 in which the halide salt soluble in the nitrogen base is lithium chloride or lithium bromide.

4. A process according to claim 2 in which the nitrogen base is pyridine or dimethylacetamide.

5. A process for the production of acrylonitrile or methacrylonitrile which comprises reacting allylamine or methallylamine with molecular oxygen in the presence of a solution in pyridine of cuprous chloride and a lithium halide selected from lithium chloride and lithium bromide, in a cuprous chloride to lithium halide ratio of from 10:1 to 1:10, at a temperature of from 0° to 200°C and at atmospheric pressure or above.

6. A process according to claim 5 in which the reaction is performed at a pressure of up to 500 p.s.i.

7. A process according to claim 5 in which the reaction is performed at a temperature of from 25° to 75°C.

8. A process according to claim 5 in which the oxidation reaction is carried out at a pressure of from 100 to 400 p.s.i. and a temperature of 25° to 75°C. in the presence of a solution in pyridine of a major weight proportion of cuprous chloride and a minor weight proportion of lithium chloride or lithium bromide.

* * * * *